United States Patent
Zhang

(10) Patent No.: US 8,763,468 B2
(45) Date of Patent: Jul. 1, 2014

(54) ELECTRODE DEVICE, PRESSURE SENSOR AND PRESSURE METER

(75) Inventor: Nianping Zhang, Shenzhen (CN)

(73) Assignee: Shenzhen Kingyield Technology Co., Ltd., Shenzhen (CN)

(*) Notice: Subject to any disclaimer, the term of this patent is extended or adjusted under 35 U.S.C. 154(b) by 280 days.

(21) Appl. No.: 13/249,552

(22) Filed: Sep. 30, 2011

(65) Prior Publication Data
US 2012/0079885 A1   Apr. 5, 2012

(30) Foreign Application Priority Data
Sep. 30, 2010 (CN) .......................... 2010 1 0298752

(51) Int. Cl.
*G01L 9/12* (2006.01)
(52) U.S. Cl.
USPC .............................................. 73/724; 73/718
(58) Field of Classification Search
None
See application file for complete search history.

(56) References Cited

U.S. PATENT DOCUMENTS

| 6,718,827 B1 | 4/2004 | Lee et al. | |
| 2006/0081052 A1* | 4/2006 | Silverbrook et al. | 73/724 |
| 2007/0283763 A1* | 12/2007 | Silverbrook et al. | 73/724 |

FOREIGN PATENT DOCUMENTS

| CN | 1932460 | 3/2007 |
| JP | 6307959 | 11/1994 |

OTHER PUBLICATIONS

English Abstract of Japanese Patent JP 6,307,959 (2 pages).
English Abstract of Chinese Patent CN 1,932,460 (1 page).

* cited by examiner

*Primary Examiner* — Andre Allen
(74) *Attorney, Agent, or Firm* — Leason Ellis LLP

(57) ABSTRACT

Provided are an electrode device, a pressure sensor and an electronic pressure meter. The electrode device may comprise: an electrode portion; and an elastically deformable portion arranged on a radial peripheral of the electrode portion. The electrode portion is integrated with the elastically deformable portion such that when a force is applied to the electrode device, the elastically deformable portion can be deformed correspondingly and the electrode portion can be displaced axially.

14 Claims, 7 Drawing Sheets

ELECTRODE DEVICE, PRESSURE SENSOR AND PRESSURE METER

TECHNICAL FIELD

The present application relates to an electrode device, a pressure sensor and a pressure measuring device. In particular, this application relates to an electrode device of an electrostatic capacity type pressure sensor, a pressure sensor, and a pressure meter which uses the pressure sensor and is especially suitable for measuring blood pressure.

BACKGROUND

Currently, pressure sensors used in electronic blood pressure meters include a semiconductor silicon type pressure sensor and a variable electrostatic capacity type pressure sensor.

A typical electrostatic capacity type pressure sensor was disclosed in a Japanese patent entitled Manufacture of Capacitive Pressure Sensor, with the publication number of JP6307959. As shown in FIG. 1, the conventional electrostatic capacity type pressure sensor comprises a base 10, an air nozzle 11 and a diaphragm plate 12 (elastic member) which are fixed on the base 10, a fixed electrode plate 15 fixed on the base 10, and a movable electrode plate 14 arranged to be parallel to the fixed electrode plate 15. The movable electrode plate 14 and the diaphragm plate 12 (elastic member) are of an up-down structure, and the movable electrode plate 14 is assembled on the diaphragm plate 12, such as by soldering.

The present inventor filed a Chinese patent entitled Electrostatic Capacity Type Pressure Sensor and Blood Pressure Meter using the same, with the publication number of CN1932460. As shown in FIGS. 2 and 3, a pressure sensor disclosed in the Chinese patent application comprises a base assembly 21, a diaphragm plate 22, a movable electrode 23 and a fixed electrode (not shown), wherein the base assembly 21 is an integrated hardware part including an air nozzle 21c, a base 21b and a movable electrode terminal 21a, and the movable electrode 23 is assembled on the diaphragm plate 22, such as by soldering.

Similarly, a typical electrostatic capacity type pressure sensor is disclosed in a US patent entitled CENTER-MOUNT CAPACITIVE SENSOR WITH OVERLOAD PROTECTION, with the patent number of U.S. Pat. No. 6,718,827B1. In this patent, capacitor plate 60 and elastic member 20 are of an up-down structure connected by fixed post 50.

In the prior art, on one hand, the capacitor plate and elastic member need to be manufactured separately, and on the other hand, when the sensor needs to be microminiaturized, there may have difficulty in connecting the capacitor plate with the elastic member of such microminiaturized up-down structure. For example, the difficulty in assembling the thin diaphragm plate with the small movable electrode will prevent the improvement of the production efficiency of the sensor. Moreover, the assembly error between the diaphragm plate and the movable electrode may also cause parallel errors and distance errors between the fixed electrode and the movable electrode of the sensor, which may affect the linearity, thus impacting the accuracy of the sensor.

SUMMARY

According to an aspect of the present application, an electrode device is provided. The electrode device may comprise an electrode portion and an elastically deformable portion arranged on the electrode portion radially. The electrode portion may be integrated with the elastically deformable portion, such that when a force is applied to the electrode device, the elastically deformable portion can deform correspondingly and the electrode portion is displaced axially.

According to another aspect of the present application, a pressure sensing device is provided. The pressure sensing device may comprise a base, an air nozzle arranged on the base, and a pressure sensing element. The pressure sensing element may comprise an electrode portion and an elastically deformable portion arranged on the electrode portion radially. The electrode portion may be integrated with the elastically deformable portion, such that when a force is applied to the pressure sensing element, the elastically deformable portion can deform correspondingly and the electrode portion is displaced axially. The pressure sensing element may hermetically fixed to the base through the elastically deformable portion. The pressure sensing element may further comprise an air chamber that can accommodate air is formed among the electrode portion, the elastically deformable portion and the base, and the air chamber may be communicated with the air nozzle.

According to yet another aspect of the present application, an electrostatic capacity type pressure sensor is provided. The electrostatic capacity type pressure sensor may comprise a fixed electrode and a pressure sensing device. The pressure sensing device may comprise a base, an air nozzle arranged on the base, and an electrode device. The electrode device may comprise an electrode portion and an elastically deformable portion arranged on the electrode portion radially. The electrode portion may be integrated with the elastically deformable portion, such that when a force is applied to the electrode device, the elastically deformable portion can deform correspondingly and the electrode portion is displaced axially. The electrode device may be hermetically fixed to the base through the elastically deformable portion. One side of the electrode portion may be arranged to be parallel to the fixed electrode, and the other side of the electrode portion, the elastically deformable portion and the base may form an air chamber that can accommodate air. The air chamber may be communicated with the air nozzle.

According to yet another aspect of the present application, an electronic pressure meter is provided. The electronic pressure meter may comprise an electrostatic capacity type pressure sensor and a microprocessor. The electrostatic capacity type pressure sensor may comprise a fixed electrode and a pressure sensing device. The pressure sensing device may comprise a base, an air nozzle arranged on the base, and an electrode device. The electrode device may comprise an electrode portion and an elastically deformable portion arranged on the electrode portion radially. The electrode portion may be integrated with the elastically deformable portion, such that when a force is applied to the electrode device, the elastically deformable portion can deform correspondingly and the electrode portion is displaced axially. The electrode device may be hermetically fixed to the base through the elastically deformable portion. An air chamber that can accommodate air may be formed between the electrode device and the base. One side of the electrode portion may be arranged to be parallel to the fixed electrode, and the other side of the electrode portion, the elastically deformable portion and the base may form an air chamber that can accommodate air. The air chamber may be communicated with the air nozzle. Electrostatic capacity signals between the electrode portion and the fixed electrode may be input to the microprocessor.

Furthermore, a part of the electrode portion may function at least as the electrode plate of an electrode of a variable capacitor.

Furthermore, the thickness of the electrode portion may be designed to makes it possible that there is no deformation on the electrode portion or the deformation of the electrode portion is within an allowed range when the force applied to the electrode portion is less than a preset value.

Furthermore, the shape of the cross-section (A-A) of the elastically deformable portion may have a structure of curve shape, corrugated shape, zigzag shape, or step shape or have a mixed structure thereof.

Furthermore, the thickness of the elastically deformable portion may be less than the thickness of the electrode portion, and the elastically deformable portion may be formed by using stamping technique to thin a portion to be stamped.

Furthermore, the electrode device may be provided with an electrode fixing portion located on peripheral of the elastically deformable portion, and the electrode device may be hermetically fixed to the base through the electrode fixing portion.

The air nozzle may be formed by extending integrally from the middle of the base; an electrode terminal is also comprised which is integrated with the air nozzle and the base.

According to yet another aspect of the present application, a method for manufacturing an electrostatic capacity type pressure sensor is provided. The method may comprise the following steps.

Step 1: manufacturing a base, and extending outwardly an air nozzle from the base in order to form an incorporate base assembly;

Step 2: reserving an electrode with a desired shape on an electrode plate, wherein the electrode functions as an electrode portion for sensing a pressure;

Step 3: processing an elastically deformable portion on the electrode plate at the peripheral of the reserved electrode, such that the elastically deformable portion can deform when the pressure acting on the electrode changes;

Step 4: hermetically fixing the electrode to the base through the elastically deformable portion, and forming an air chamber that can accommodate air by the electrode, the elastically deformable portion and the base;

Step 5: manufacturing a fixed electrode with a desired shape; and

Step 6: aligning the electrode with the fixed electrode to fix them together in a parallel manner, such that when a pressure of air entering into the air chamber from the air nozzle is changed, a distance between the electrode and the fixed electrode can be changed due to a deformation of the elastically deformable portion, such that an electrostatic capacity of the pressure sensor can be changed.

Furthermore, the step of processing an elastically deformable portion may comprise using stamping technique to thin a portion to be stamped, and causing the shape of processed cross-section (A-A) of the elastically deformable portion to have a structure of curve shape, corrugated shape, zigzag shape, or step shape or have a mixed structure thereof.

As the electrode device according to the present application may comprise an electrode portion and an elastically deformable portion integrated with the electrode portion radially, such that when a force is applied to the electrode device, the elastically deformable portion can deform correspondingly and the electrode portion is displaced axially. Accordingly, the electrode device is a mechanical device which can also function as an electrode plate of a variable capacitor and thus be an electronic device. In other words, the electrode device has both mechanical and electronic functions. It needs no assembly between the electrode portion and the elastically deformable portion, such that a series of technical problems caused by the assembly between the electrode device and the diaphragm plate in the prior art are avoided skillfully, in addition, there is no assembly errors, the assembly procedure is simpler, the fixing accuracy is high, and the manufacturing efficiency of the sensor can be improved.

DRAWINGS

Electrostatic capacity type pressure sensors in the present application will now be described in detail, with reference to the appended drawings, in which.

DETAILED DESCRIPTION

In order to describe the implementation of the present application clearly, the terms "axial direction" and "radial direction" are respectively defined as follows.

Axial direction refers to a direction perpendicular to the surface of the plate.

Radial direction refers to a direction perpendicular to the axial direction.

Example 1

Figure 1:
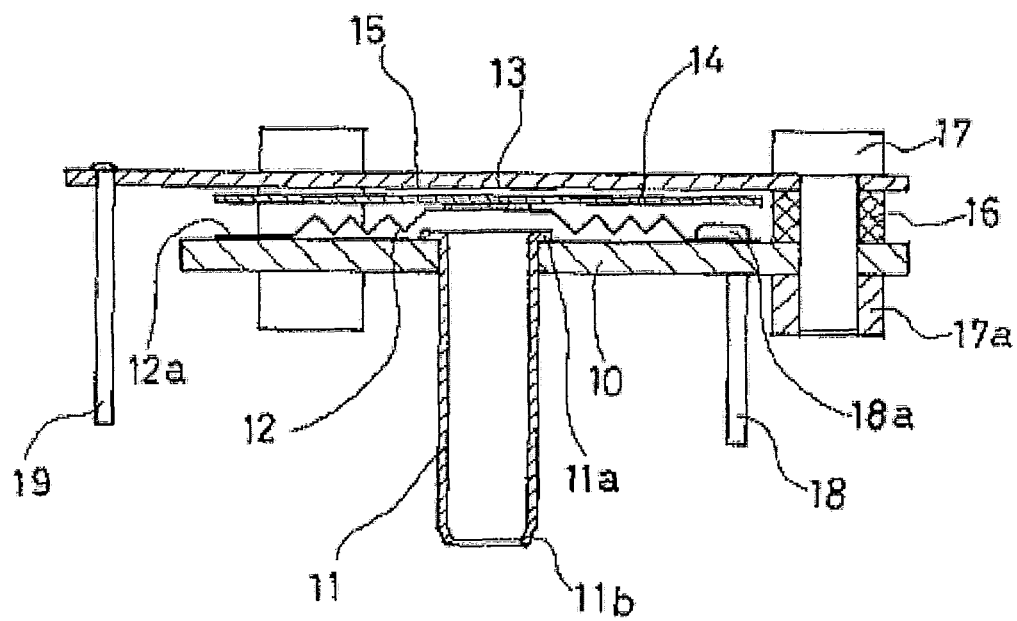
FIG. 1 is a structural representation of an electrostatic capacity type pressure sensor in prior art.
Figure 2:
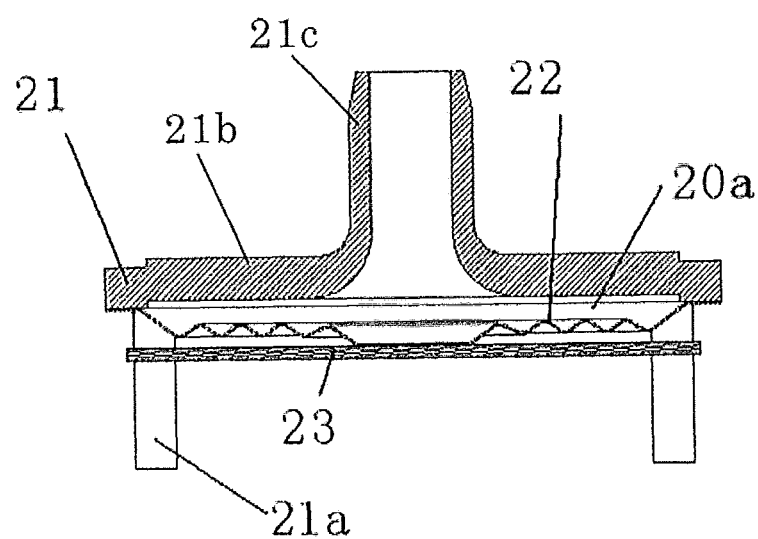
FIG. 2 is a structural representation of another electrostatic capacity type pressure sensor in prior art.
Figure 3:
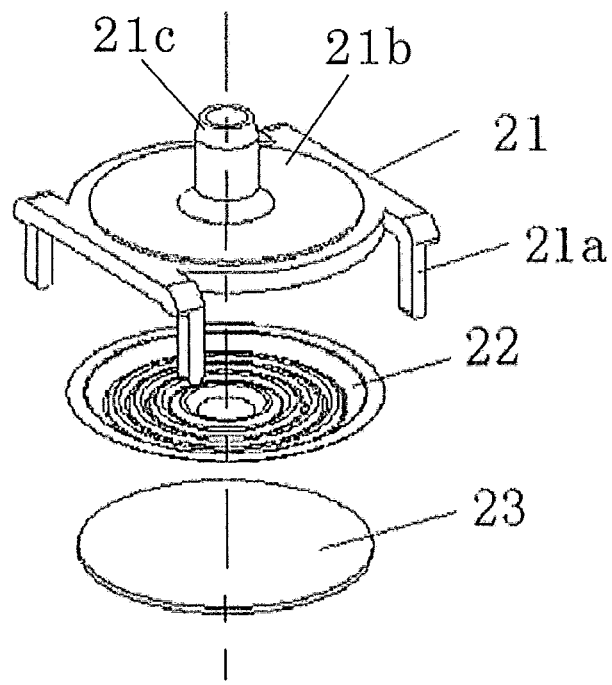
FIG. 3 is an exploded view of FIG. 2.
Figure 4:
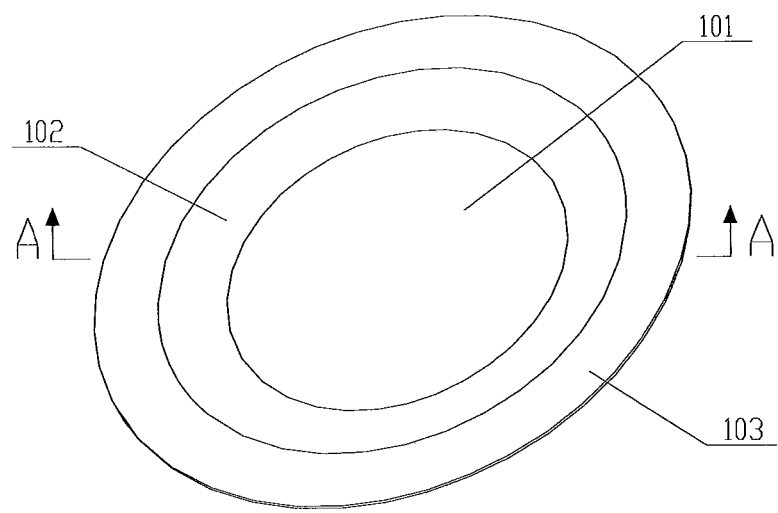
FIG. 4 is a structural representation of an electrode device of an electrostatic capacity type pressure sensor.
Figure 5:
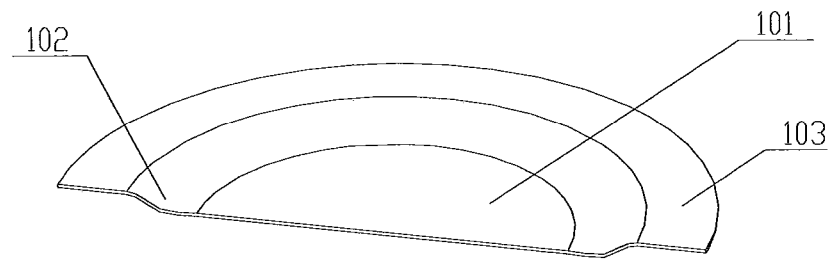
FIG. 5 is a section view of FIG. 4 taken along A-A.

In an embodiment, an electrode device of a variable capacitor, as shown in FIGS. 4 and 5, comprises an electrode portion 101 and an elastically deformable portion 102 arranged on radial peripheral of the electrode portion 101. It will be understood that the elastically deformable portion 102 can be positioned at a same plane with the electrode portion 101 or the elastically deformable portion 102 can be positioned at a plane at an angle with the plane at which the electrode portion 101 is positioned. The electrode device shown in FIGS. 4 and 5 may also comprise a fixing portion 103 for fixing the electrode device. The electrode portion 101, the elastically deformable portion 102 and the fixing portion 103 may be an integral structure formed by one-time processing. Optionally, the electrode portion 101 and the elastically deformable portion 102 may be integrated in other manners. The electrode portion 101 may have a relatively large thickness which should ensure that there is no deformation on the electrode portion 101 or the deformation of the electrode portion 101 does not go beyond an allowed range when the force applied to the electrode portion is not more than a preset value. The shape of the cross-section of the elastically deformable portion 102 (i.e. a cross-section taken along a radial line A-A) may have a curve structure. Compared to the electrode portion 101, the structure of the elastically deformable portion 102 should be processed to be thinner than the electrode portion 101, such that when a force is applied to the electrode device, the elastically deformable portion 102 can be deformed correspondingly and the electrode portion 101 can be displaced axially.

The electrode portion 101 can function, partly or fully, as an electrode plate for a conventional variable capacitor as required. Therefore, in the present invention, the electrode device is a mechanical device which can also be an electronic device to function as an electrode plate of a variable capacitor. In other words, the electrode device has both mechanical and electronic functions.

An embodiment of manufacturing the electrode device described herein may comprise the following steps:

Step 1: retaining an area with a desired shape on an electrode plate as an electrode portion 101; and Step 2: decreasing a thickness by stamping or other processing, and forming a determined shape of the electrode plate at a radial peripheral of the electrode portion 101 to form an elastically deformable portion 102, such that the elastically deformable portion 102 can be deformed correspondingly and the electrode portion 101 can be displaced axially when the pressure acting on the electrode device changes.

Example 2

Figure 6:
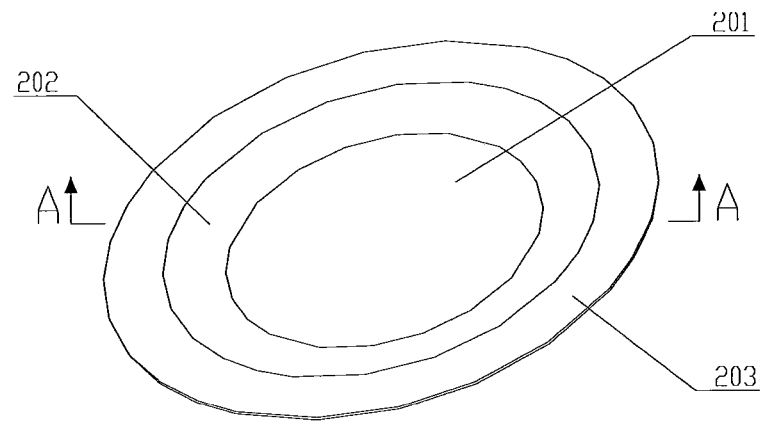
FIG. 6 is a structural representation of another electrode device of an electrostatic capacity type pressure sensor.
Figure 7:
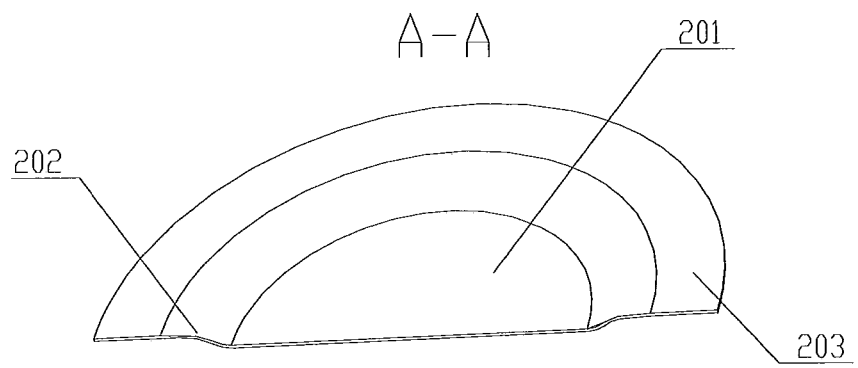
FIG. 7 is a section view of FIG. 6 taken along A-A.

In another embodiment of the electrode device of a variable capacitor, with reference to FIGS. 6 and 7, it comprises an electrode portion 201, an elastically deformable portion 202, and a fixing portion 203. The shape of a cross-section of the elastically deformable portion 202 taken along a radial line A-A according to this example is different from that of example 1. Specifically, the shape of the cross-section of the elastically deformable portion 102 in Example 1 is protruding outwardly (i.e. the elastically deformable portion 102 has a curve surface protruding outwardly), but the elastically deformable portion 202 in this example is protruding inwardly (i.e. the elastically deformable portion 202 has a curve surface protruding inwardly). The rest of the structure and a manufacturing method therefor according to this example are similar to those of Example 1.

It is understood by those skilled in the art that, in order to deform the elastically deformable portion when it is under force, the elastically deformable portion can employ the combination of the curve surface of example 1 and the curve surface of example 2. That is to say, the elastically deformable portion can have a curve surface with corrugated shape. Accordingly, the shape of the cross-section of the elastically deformable portion can have a structure of corrugated shape. Furthermore, in order to deform the elastically deformable portion when it is under force, in addition to employing a curve surface structure, the shape of the cross-section of the elastically deformable portion can have a structure of other nonlinear shapes, such as a step shape, and a zigzag shape.

Example 3

Figure 8:
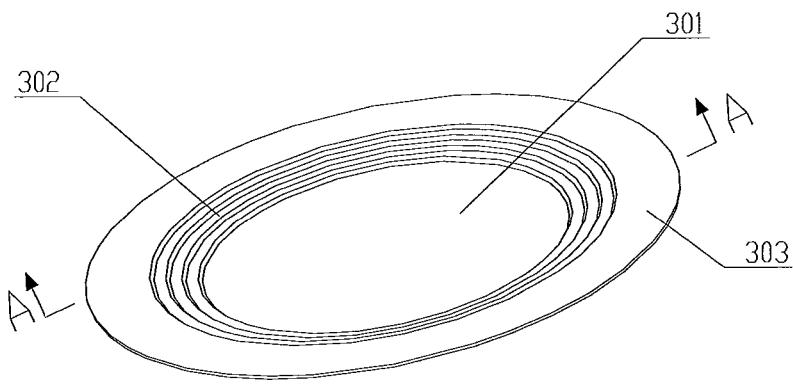
FIG. 8 is a structural representation of yet another electrode device of an electrostatic capacity type pressure sensor.
Figure 9:
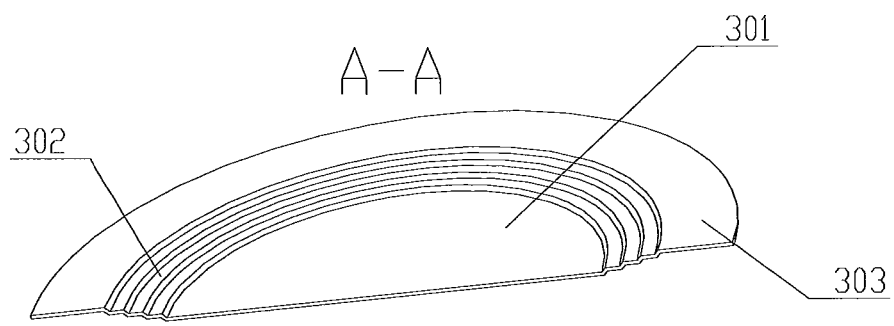
FIG. 9 is a section view of FIG. 8 taken along A-A.

Yet another electrode device of a variable capacitor, with reference to FIGS. 8 and 9, comprises an electrode portion 301, an elastically deformable portion 302, and a fixing portion 303. The shape of a cross-section of the elastically deformable portion 302 taken along a radial line A-A according to this example is different from that of example 1. In the present example, the elastically deformable portion has a cross-section with a step shape. During manufacturing of the elastically deformable portion 302, the portion to be processed can be stamped to have a structure of step shape. The rest of the structure and a manufacturing method according to this example are similar to those of Example 1.

Example 4

Figure 10:
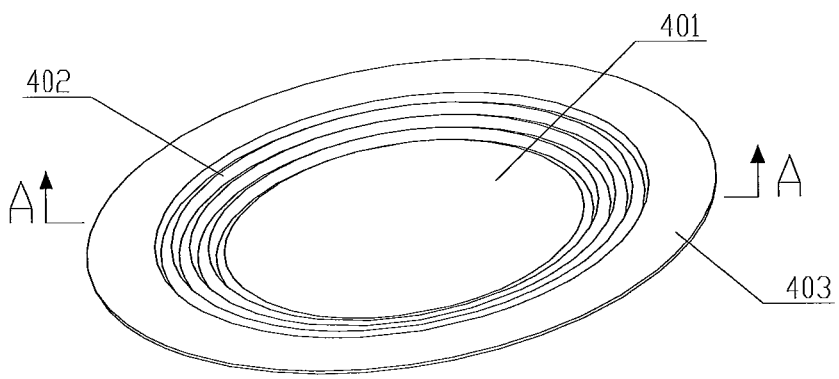
FIG. 10 is a structural representation of yet another electrode device of an electrostatic capacity type pressure sensor.
Figure 11:
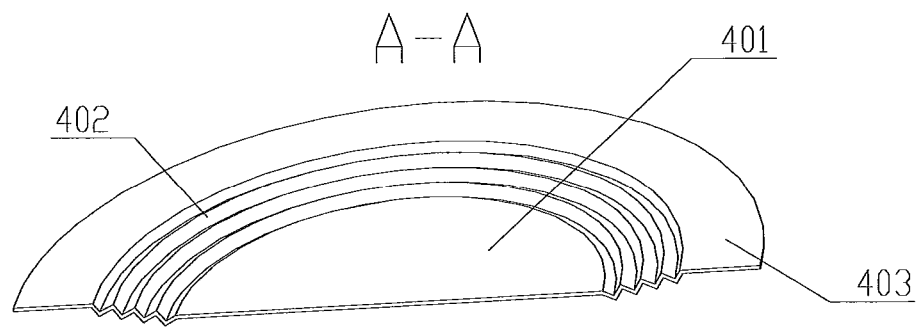
FIG. 11 is a section view of FIG. 10 taken along A-A.
Figure 12:
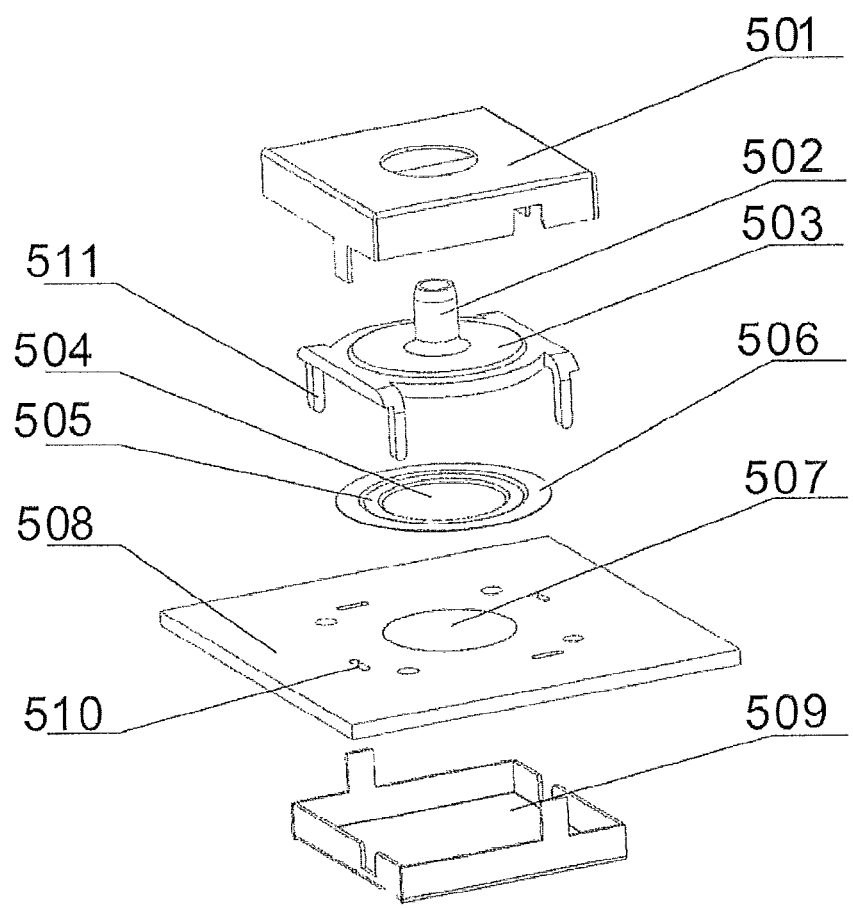
FIG. 12 is an exploded view of an electrostatic capacity type pressure sensor.
Figure 13:
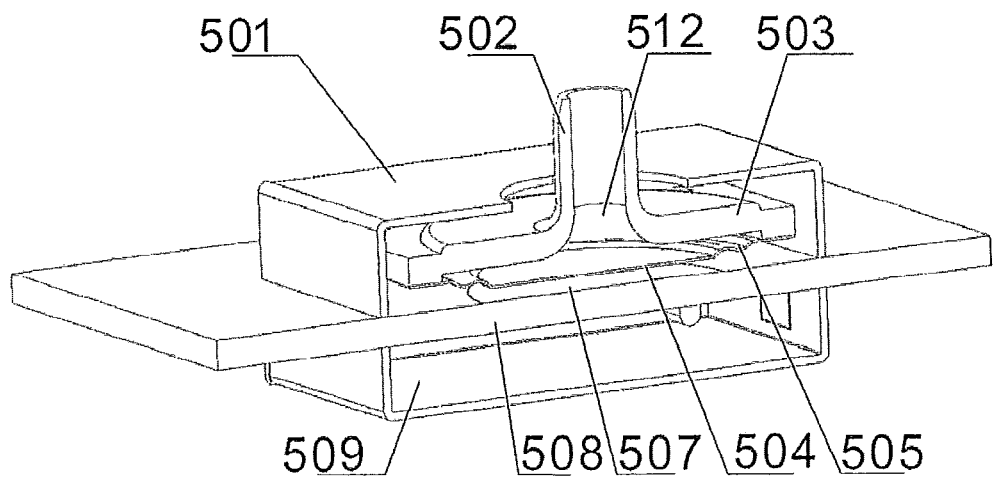
FIG. 13 is an assembly structural representation of FIG. 12.
Figure 14:
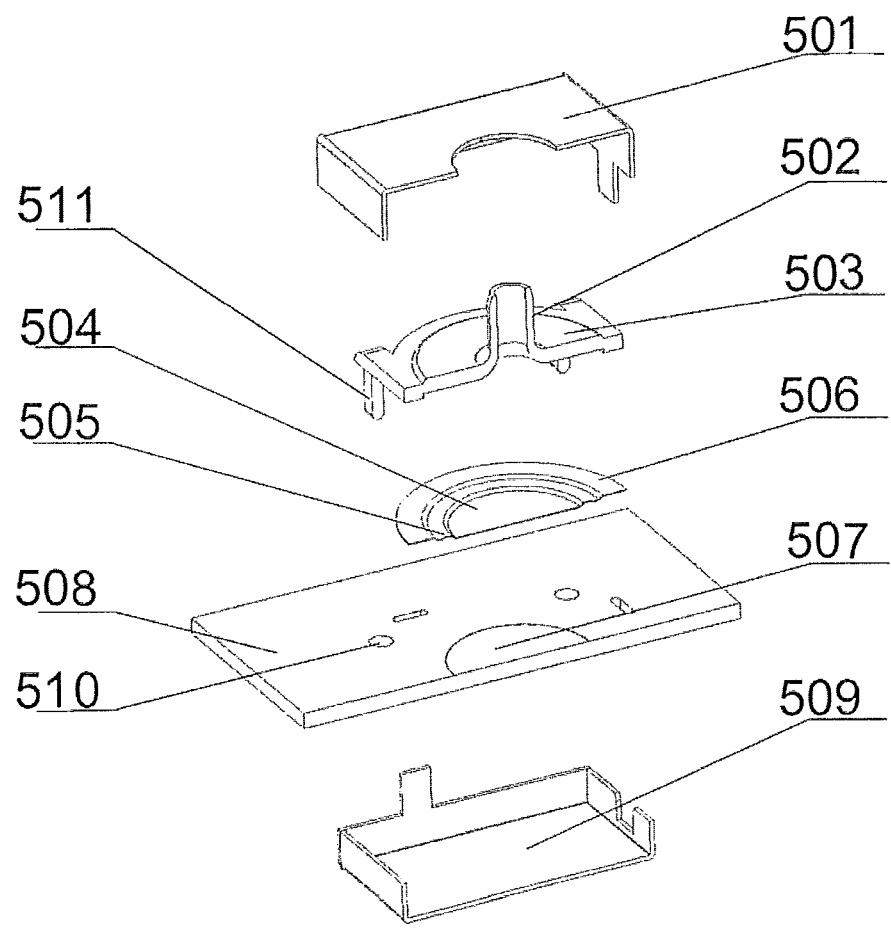
FIG. 14 is a portion section view of FIG. 12.

Yet another electrode device of a variable capacitor, with reference to FIGS. 10 and 11, comprises an electrode portion 401, an elastically deformable portion 402, and a fixing portion 403. The shape of a cross-section of the elastically deformable portion 402 taken along a radial line A-A according to this example is different from that of example 1. In this example, the elastically deformable portion substantially presents a cross-section with a zigzag shape. During manufacturing of the elastically deformable portion 402, the portion to be processed can be stamped to have a structure of zigzag shape. The rest structure and the manufacturing method according to this example are similar to those of example 1.

Example 5

An electrostatic capacity type pressure sensor, with reference to FIGS. 12 to 15, comprises an upper shielding case 501, a pressure sensing device, a fixed electrode 507 and a lower shielding case 509. The pressure sensing device comprises an air nozzle 502, a base 503, an electrode device and an electrode terminal 511. The electrode device comprises an electrode portion 504, an elastically deformable portion 505 arranged on radial peripheral of the electrode portion 504 and a fixing portion 506. The electrode portion 504, the elastically deformable portion 505 and the fixing portion 506 may be an integral structure formed by one-time processing. The thickness of the electrode portion 504 should ensure that there is no deformation on the electrode portion 504 or the deformation of the electrode portion 504 does not go beyond an allowed error range when the force applied to the electrode portion 504 is not more than a preset value (for example, the maximum value of the pressure that can be detected by the pressure sensor). The shape (FIG. 14) of the cross-section of the elastically deformable portion 505 substantially presents a curve of corrugated shape. Comparing to the electrode portion 504, the structure of the elastically deformable portion 505 should be processed to be thinner than the electrode portion 504, such that when a force is applied to the electrode device, the elastically deformable portion 505 can be deformed correspondingly and the electrode portion 504 can be displaced axially. An electrode fixing portion 506 is arranged at the radial peripheral of the elastically deformable portion 505. The electrode portion 504 is hermetically fixed to the base 503 through the electrode fixing portion 506. One side of the electrode portion 504, the elastically deformable portion 505, the electrode fixing portion 506 and the base 503 form an air chamber 512 that can accommodate air, wherein the air chamber 512 is communicated with the air nozzle 502. The fixed electrode 507 can be manufactured on the copper foil of a printed circuit board 508, and one or more mounting holes 510 can be provided on the printed circuit board 508 around the fixed electrode 507. One end of the electrode terminal 511 is electrically connected to the electrode portion 504, and the other end of the electrode terminal 511 is inserted into the electrode terminal mounting hole 510 in a fixed manner. The other side of the electrode portion 504 is aligned with the fixed electrode 507 on the printed circuit board 508 and is arranged to be parallel to the fixed electrode 507. The pressure sensing device and the fixed electrode 507 is arranged between the snapped upper shielding case 501 and lower shielding case 509, in order to avoid the outside electromagnetic interference.

In operation, when air entering into the air chamber 512 creates a pressure acting on the electrode device to change, the elastically deformable portion 505 is deformed, so as to change the distance between the electrode portion 504 and the fixed electrode 507, which in turn changes the electrostatic capacity of the pressure sensor.

A method for manufacturing the above-mentioned electrostatic capacity type pressure sensors may comprise the following steps.

Step 1: manufacturing a base 503 with a conductive material, and forming an air nozzle 502 and an electrode terminal 511 extending outwardly from the base 503 in order to form an integral base assembly;

Step 2: retaining an area with a desired shape on an electrode plate as an electrode portion 504;

Step 3: forming an elastically deformable portion 505 with for example corrugated shape by processing the electrode plate at the radial peripheral of the electrode portion 504 through for example stamping or other processing, and retaining an area on the electrode plate at the radial peripheral of the elastically deformable portion 505 to form a fixing portion 506;

Step 4: hermetically fixing the electrode portion 504 to the base 503 through the fixing portion 506, and forming an air chamber 512 that can accommodate air;

Step 5: manufacturing a fixed electrode 507 with a predetermined shape on the copper foil of a printed circuit board 508; and Step 6: opening a mounting hole 510 on the printed circuit board 508 around the fixed electrode 507, wherein one end of the electrode terminal 511 is electrically connected to the electrode portion 504, and the other end of the electrode terminal 511 is inserted into the electrode terminal mounting hole 510 in a fixed manner, and wherein a side of the electrode portion 504 is aligned with the fixed electrode 507 on the printed circuit board 508 and is arranged to be parallel to the fixed electrode 507.

It is understood by those skilled in the art that the electrode device of the electrostatic capacity type pressure sensor in this example may employ any one of the structures described in Examples 1 to 4, and in addition to the structure of a curve shape, corrugated shape, zigzag shape, or step shape, the shape of the cross-section of the elastically deformable portion taken along the radial line (A-A) can employ a combination of them as required.

Example 6

Figure 15:
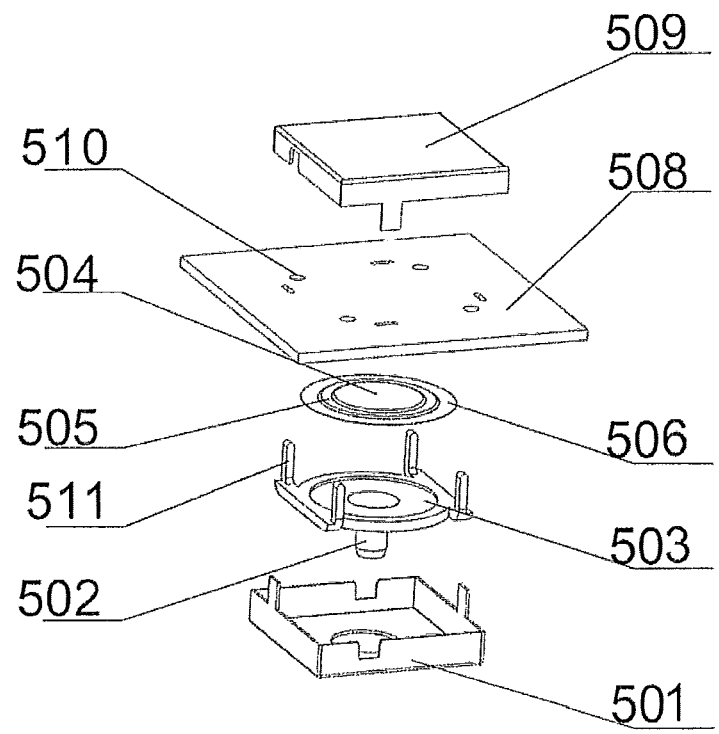
FIG. 15 is an exploded view of FIG. 12 in reverse.
Figure 16:
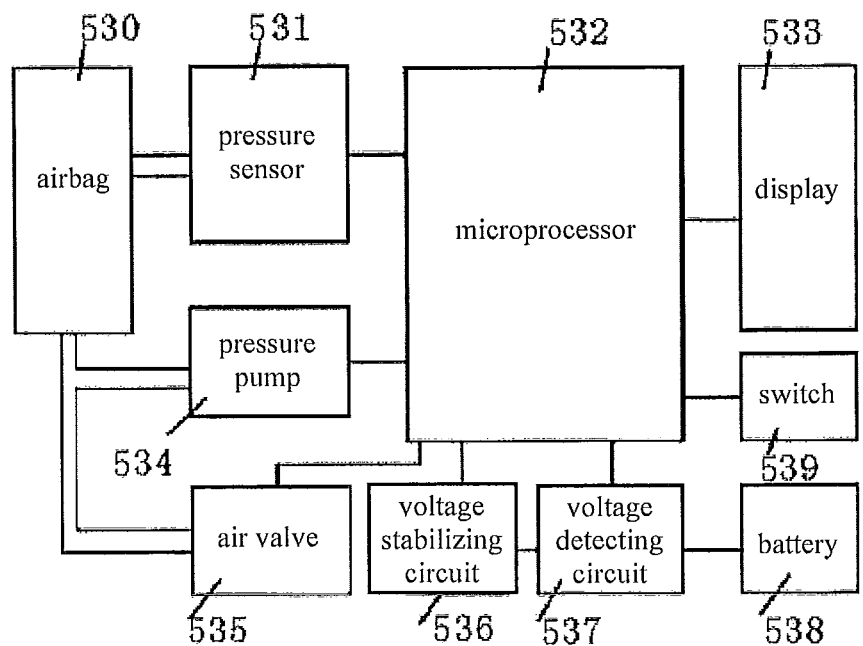
FIG. 16 is a block diagram of an electronic blood pressure measuring device using the electrostatic capacity type pressure sensor according to the invention.

An electronic pressure meter, with reference to FIGS. 15 and 16, comprises an airbag 530, a pressure sensor 531, a pressure pump 534, an air valve 535, a battery 538, a voltage detecting circuit 537, a voltage stabilizing circuit 536, a microprocessor 532, a display 533 and a switch 539. The airbag 530, the pressure pump 534, the air valve 535, the battery 538, the voltage detecting circuit 537, the voltage stabilizing circuit 536, the microprocessor 532, the display 533 and the switch 539 are well known in the prior art. The microprocessor 532 can calculate and output a blood pressure reading according to the input of the pressure sensor 531. The pressure sensor employs the structure of the electrostatic capacity type pressure sensor described in example 5, in which a printed circuit board 508 is the main circuit of the blood pressure meter. The top of the nozzle 502 is communicated with the airbag 530, and the electrostatic capacity signals produced due to the pressure variation and detected by the electrode portion 504 and the fixed electrode 507 can be inputted to the microprocessor 532 via the electrode terminal 511 and the printed circuit board 508 connected to the fixed electrode 507.

It is understood by those skilled in the art that, in addition to the implementation in a blood pressure measurement, the present invention can be used in other types of air pressure measurements. Similarly, the present invention can be used in measuring hydraulic pressure changes, and can be suitable for any types of pressure measurements.

Hereinabove, illustrative embodiments according to the present application are described with reference to the accompanying drawings. However, for those skilled in the art, it is appreciated to combine different elements mentioned above forming different technical solutions.

The invention claimed is:

1. A pressure sensing device, comprising:
    a base;
    an air nozzle arranged on the base; and
    an electrode device,
    wherein the electrode device comprises an electrode portion; and an elastically deformable portion arranged on a radial peripheral of the electrode portion,
    wherein the electrode portion is integrated with the elastically deformable portion such that when a force is applied to the electrode device, the elastically deformable portion is deformed correspondingly and the electrode portion is displaced axially, and
    wherein the electrode device is hermetically fixed to the base, such that an air chamber that can accommodate air is formed between the electrode device and the base, and the air chamber is communicated with the air nozzle.

2. The pressure sensing device of claim 1, wherein a thickness of the electrode portion is designed such that there is no deformation on the electrode portion or the deformation of the electrode portion is within an allowed range when a force applied to the electrode device is less than a preset value.

3. The pressure sensing device of claim 1, wherein a cross-section of the elastically deformable portion has a curve shape, a zigzag shape, or a step shape.

4. The pressure sensing device of claim 3, wherein a thickness of the elastically deformable portion is less than a thickness of the electrode portion, and the elastically deformable portion is formed using stamping a portion to be processed to reduce a thickness of the portion to be processed.

5. An electrostatic capacity type pressure sensor, comprising:
    a fixed electrode; and
    a pressure sensing device,
    wherein the pressure sensing device comprises a base; an air nozzle arranged on the base; and an electrode device,
    wherein the electrode device comprises an electrode portion; and an elastically deformable portion arranged on a radial peripheral of the electrode portion,
    wherein the electrode portion is integrated with the elastically deformable portion such that when a force is applied to the moveable electrode device, the elastically deformable portion is deformed correspondingly and the electrode portion is displaced axially, wherein the electrode device is hermetically fixed to the base, such that an air chamber that can accommodate air is formed between the electrode device and the base, and wherein one side of the electrode portion is arranged to be parallel to the fixed electrode, and the other side of the electrode portion, the elastically deformable portion and the base form the air chamber;

wherein the air chamber is communicated with the air nozzle.

6. The electrostatic capacity type pressure sensor of claim 5, wherein a thickness of the electrode portion is designed such that there is no deformation on the electrode portion or the deformation of the electrode portion is within an allowed range when a force applied to the electrode device is less than a preset value.

7. The electrostatic capacity type pressure sensor of claim 5, wherein a cross-section of the elastically deformable portion has a shape of curve type, zigzag type, or step type.

8. The electrostatic capacity type pressure sensor of claim 5, wherein the air nozzle is extending integrally from a middle part of the base.

9. The electrostatic capacity type pressure sensor of claim 5, wherein the electrode device is further provided with a fixing portion located on a radial peripheral of the elastically deformable portion, and the electrode device is hermetically fixed to the base through the fixing portion.

10. An electronic pressure meter, comprising:
an electrostatic capacity type pressure sensor; and
a microprocessor,
wherein the electrostatic capacity type pressure sensor comprises: a fixed electrode; and a pressure sensing device,
wherein the pressure sensing device comprises: a base; an air nozzle arranged on the base; and an electrode device,
wherein the electrode device comprises: an electrode portion; and an elastically deformable portion arranged on a radial peripheral of the electrode portion, wherein the electrode portion is integrated with the elastically deformable portion such that when a force is applied to the electrode device, the elastically deformable portion is deformed correspondingly and the electrode portion is displaced axially,
wherein the electrode device is hermetically fixed to the base, such that an air chamber that can accommodate air is formed between the electrode device and the base,
wherein one side of the electrode portion is arranged to be parallel to the fixed electrode, and the other side of the electrode portion, the elastically deformable portion and the base form the air chamber, wherein the air chamber is communicated with the air nozzle, and wherein electrostatic capacity signals between the electrode portion and the fixed electrode are input to the microprocessor.

11. The electronic pressure meter of claim 10, wherein a thickness of the electrode portion is designed such that there is no deformation on the electrode portion or the deformation of the electrode portion is within an allowed range when a force applied to the electrode portion is less than a preset value.

12. The electronic pressure meter of claim 10, wherein the electrode device is further provided with a fixing portion located on a radial peripheral of the elastically deformable portion, and the electrode device is hermetically fixed to the base through the fixing portion.

13. A method for manufacturing an electrostatic capacity type pressure sensor, comprising:
forming an air nozzle extending outwardly from the base in order to form an incorporate base assembly;
retaining an area with a desired shape on an electrode plate to form an electrode portion;
forming an elastically deformable portion by processing the electrode plate at a radial peripheral of the formed electrode portion, such that when a force is applied to the electrode plate, the elastically deformable portion is deformed correspondingly and the electrode portion is displaced axially;
hermetically fixing the electrode portion to the base through the elastically deformable portion, and forming an air chamber that can accommodate air through the electrode portion, the elastically deformable portion and the base;
manufacturing a fixed electrode with a desired shape;
aligning the electrode portion with the fixed electrode to fix them together in a parallel manner, such that when a pressure of air entering into the air chamber from the air nozzle is changed, a distance between the electrode portion and the fixed electrode can be changed due to a deformation of the elastically deformable portion, such that an electrostatic capacity of the pressure sensor can be changed.

14. The method of claim 13, wherein the forming an elastically deformable portion comprises:
using stamping technique to thin a portion to be processed, wherein the elastically deformable portion has a cross-section of curve shape, corrugated shape, zigzag shape, or step shape or a mixed thereof.

* * * * *